United States Patent [19]

Chance

[11] 4,441,502

[45] Apr. 10, 1984

[54] NMR SYSTEM FOR DETERMINING RELATIONSHIP BETWEEN WORK OUTPUT AND OXIDATIVE PHOSPHORYLATION CAPABILITY IN AN EXERCISING BODY MEMBER

[76] Inventor: Britton Chance, c/o Johnson Research Foundation, School of Medicine, University of Pennsylvania, Philadelphia, Pa. 19104

[21] Appl. No.: 409,554

[22] Filed: Aug. 19, 1982

[51] Int. Cl.$^3$ ............................................. A61B 5/05
[52] U.S. Cl. ................................................... 128/653
[58] Field of Search ................ 128/653; 324/309–310

[56] References Cited

U.S. PATENT DOCUMENTS 4,354,499 10/1982 Damadian ........................ 324/309 X
4,413,233 11/1983 Fossel et al. .................... 324/309 X

OTHER PUBLICATIONS

Mansfield, P. et al., "NMR Imaging in Bio-Medicine", Academic Press, New York & London, 1982, pp. 238–242.

*Primary Examiner*—Kyle L. Howell
*Assistant Examiner*—Francis J. Jaworski
*Attorney, Agent, or Firm*—Herman L. Gordon

[57] ABSTRACT

A NMR apparatus for determining the relationship between work output of an exercising body member and the steady-state capability of oxidative phosphorylation of the muscle tissue as measured by the $PCr/P_i$ ratio in the tissue. The apparatus includes the large hollow magnet of the NMR system, with a radio frequency probe mounted therein, arranged to underlie a human limb, such as an arm, inserted in the magnet from one end. Adjacent to the opposite end a Cybex ergometer is mounted. A hand lever is pivotally mounted in the magnet and is connected by a link bar to the drive arm of the ergometer. The subject inserts his arm in the magnet and grasps the hand lever, performing controlled work strokes at uniformly spaced short intervals over a selected length of time, such as 10 minutes, observing the output trace of the ergometer and maintaining a constant work output intensity with each stroke. The NMR apparatus provides curves of the NMR response at 24.3 MHz and a magnetic field of 20 kg, showing the intensities of the phosphorus-containing components of the muscle tissue, including PCr and $P_i$. This enables accurate measurement and monitoring of the work output from the muscle simultaneously with the generation of the phosphorus NMR response curves. A curve may be plotted showing $PCr/P_i$ versus time, which affords criteria of muscle performance. Another useful curve may be plotted showing muscle unit volume work rate in terms of joules/sec versus $P_i/PCr$, also capable of detecting biochemical abnormality, muscle dystrophy or vascular disease.

8 Claims, 6 Drawing Figures

NMR SYSTEM FOR DETERMINING RELATIONSHIP BETWEEN WORK OUTPUT AND OXIDATIVE PHOSPHORYLATION CAPABILITY IN AN EXERCISING BODY MEMBER

FIELD OF THE INVENTION

This invention relates to non-invasive systems for obtaining medically and scientifically significant information from living bodies, and more particularly to an improved nuclear magnetic resonance (NMR) apparatus for determining the relationship between work output of an exercising body member and the steady-state capability of oxidative phosphorylation, as measured by the phosphocreatine/inorganic phosphate ($PCr/P_i$) ratio in the body member.

BACKGROUND OF THE INVENTION

Nuclear magnetic resonance (NMR) offers the opportunity of selectively examining the nature and function of nucleii of atoms attached to a variety of important biochemicals, of which phosphorus and carbon appear to be currently the most useful, and are pivotal in cell metabolism as well. Nuclear magnetic resonance can most simply be described as a pulsed nuclear clock, the rate of which is sensitively dependent upon the chemical environment of the particular nucleus. For example, the atoms of phosphorus, which are attached to a series of key energy-related compounds of the body, give an appropriate signature, where the important phosphate compounds in the brain, heart, kidney, liver, and skeletal tissues are the high energy compounds, ATP, the "energy currency" of the body, and creatine phosphate, PCr, the "short-term energy reserve" of the body, together with low energy forms of these compounds, adenosine diphosphate and inorganic phosphate. In addition, the sugar phosphate from the metabolic pathway activated by glucose metabolism can also be found (F6P, DPG).

In the past there have been numerous problems in applying NMR to tissue under the proper conditions, and in collecting and interpreting the resultant electrical data. In particular, previously proposed methods for determining the relationship between work output from an exercising body member, using the NMR technique, have been unsatisfactory because they do not employ a reliable means for accurately measuring the work output.

SUMMARY OF THE INVENTION

Reference is made to the pending patent application of Britton Chance et al, Ser. No. 373,283, filed Apr. 29, 1982, entitled "NMR System for the Non-Invasive Study of Phosphorus Metabolism" which provides detailed electrical information relating to the basic construction of a NMR apparatus suitable for employment in conjunction with the apparatus of the present invention.

In a typical technique according to the present invention, phosphorus NMR is used to determine the relationship between work output in the exercising human forearm and the steady-state capability of oxidative phosphorylation, as measured by the phosphocreatin/inorganic phosphate ($PCr/P_i$) ratio. Experimentally, exercise intensities comprising uniformly periodic contractions for a reasonable period, such as somewhat less than one hour, produced ratios of about 1.0 for a subject of moderate training. Linear relationships between work rate per unit of muscle volume and the $P_i/PCr$ values were found for the subject's left and right arms. The system affords sensitive criteria of muscle performance in normal subjects, and of biochemical or vascular disease in abnormal subjects. The $P_i$, PCr and ATP levels found by the phosphorus NMR technique represent the average of the time-varying values over the cycle of contraction and relaxation which permit the restitution of a resting state prior to the next contraction and the continuation of work performance.

The general technique of the present invention consists in placing the body member (for example, an arm or leg) in the uniform-field region of the NMR magnet and drivingly coupling the member to a work-measuring device, such as a Cybex ergometer, the tissue under study being maintained in contact with the transceiver probe coil of the NMR apparatus. For example, where a human arm is to be investigated, such as to involve the measurement of the work output of the wrist flexor muscle, the Cybex ergometer is mechanically coupled to the wrist muscle via a non-magnetic hand lever and a non-magnetic linkage. Wrist-flexor work output is recorded, while PCr and $P_i$ are measured in the forearm musculature, which overlies the NMR probe inside the magnet.

The subject performs contractions at a regular periodic rate, for example, in response to a periodic audible signal from the associated computer, and may observe the intensity of the contractions (output signals of the Cybex ergometer) on an oscilloscope and control his work efforts in a manner to maintain the visible signals uniform in amplitude. A preliminary "warm up" period may be employed to allow for circulatory adjustments. The free induction decays (FID) which contains the information concerning the amounts and types of P-containing compounds present in the muscle, are gated for an interval of 100 msec at the end of each muscular contraction, and prior to relaxation.

The characteristic spectra of the P-containing compounds present in the muscle are recorded at regular intervals, typically wherein the muscle is contracted every five seconds over the selected period of the test, for example, 10 minutes, and the PCr and $P_i$ values may be employed to plot respective curves of $PCr/P_i$ vs. exercise time and work rate vs $P_i/PCr$, thereby providing significant indications of the relationship between muscular activity and mitochondrial metabolic state of the patient's muscle tissue.

Accordingly, a main object of the invention is to provide an improved non-invasive method and apparatus for studying the relationship between the activity of the musculature of a living body member and the activity of the mitochondria associated with the metabolism in said musculature.

A further object of the invention is to provide an improved NMR test apparatus for studying the relationship between the metabolism and the work rate of a living body member and to determine metabolic deficiencies such as would be associated with abnormal or pathological conditions in the body member.

A still further object of the invention is to provide an improved NMR test apparatus for use in determining metabolic deficiencies in a living body member which cause unusual changes in $PCr/P_i$ responses to work, and to evaluate deficits in the function of mitochondrial energy metabolism and in the efficiency of myofibrils associated with the body member, facilitating diagnosis of such deficits as peripheral vascular flow decrease causing diminished oxygen delivery and oxidative phosphorylation, or an enzymatic defect in the energy-conserving system which would cause muscular dystrophies affecting the myofibrils if not the metabolic system.

A still further object of the invention is to provide an improved NMR test apparatus for studying the relationship between the metabolism and work rate of a living body member, the apparatus allowing the insertion of the body member into the NMR magnet and the engagement of the body member with the transceiver probe of the apparatus in a region of uniform field strength in the magnet, and including a manipulatory member coupled to an external ergometer for enabling the body member to drive the ergometer in a manner subjecting the musculature of the body member to a known amount of work at a known reproducible rate for a definite period of time, to thereby provide a measurable, accurately controlled work output value which can be utilized in computing the relationship between the performed work and the $P_i/PCr$ ratio associated with said body member in the study.

BRIEF DESCRIPTION OF THE DRAWINGS

Further objects and advantages of the invention will become apparent from the following description and claims, and from the accompanying drawings, wherein:

DETAILED DESCRIPTION OF A PREFERRED EMBODIMENT

Figure 1:
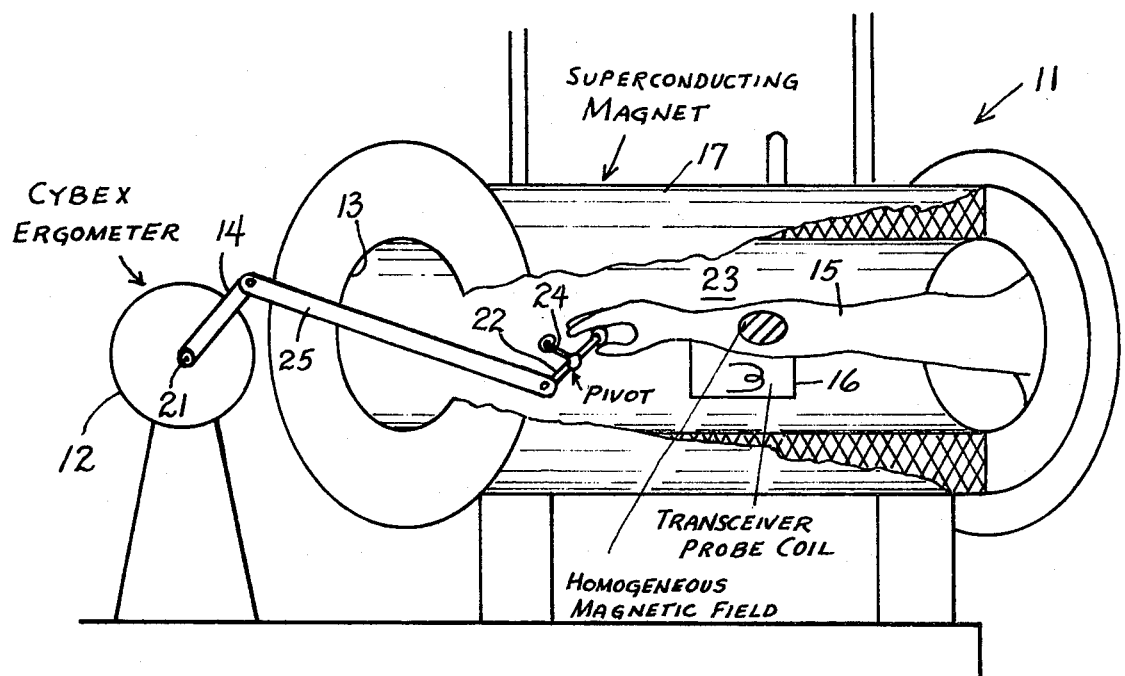
FIG. 1 is a diagrammatic perspective view, partly broken away, showing a human arm resting on a probe in a homogeneous magnetic field of a nuclear magnetic resonance analytical apparatus provided with means for subjecting the arm to a known amount of work in a system according to the present invention, said means comprising a Cybex ergometer.
Figure 3A:
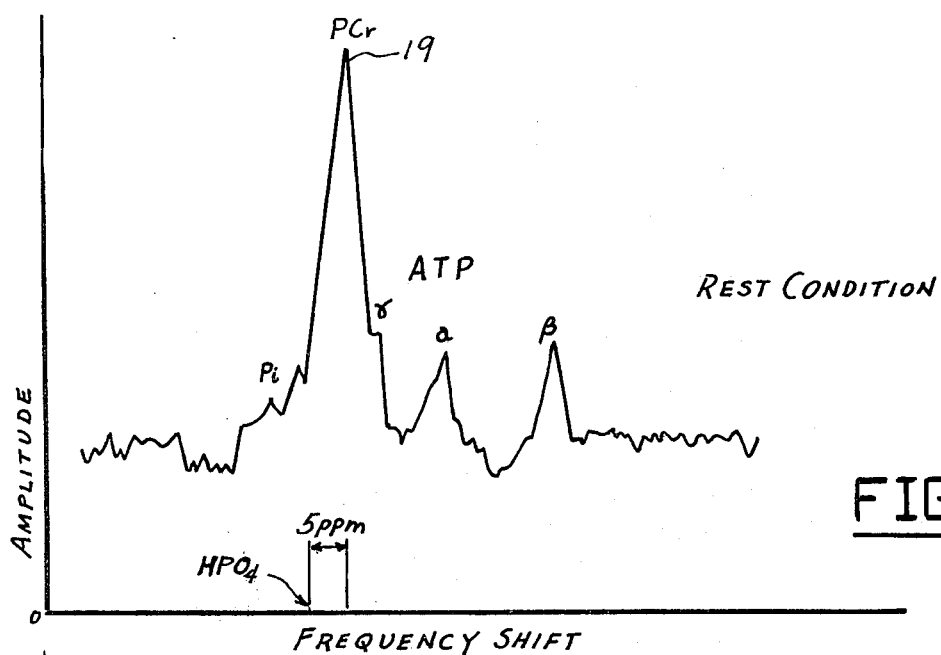
FIGS. 3A and 3B are respective curves obtainable from the analytical NMR system of FIG. 1, depicting the intensities of the phosphorus-containing components of the human arm for the rest condition of the human arm, and for the condition after a period of actuation of the ergometer.
Figure 3B:
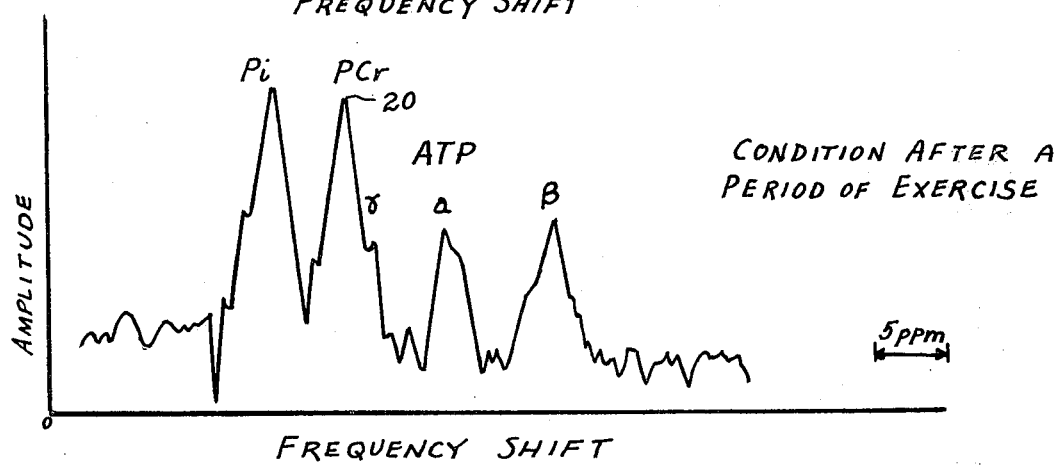

Referring to the drawings, FIG. 1 is a diagrammatic view of a human arm 15 resting on the probe 16 of a nuclear magnetic resonance analytical apparatus, shown generally at 11, the apparatus 11 being equipped with a suitable ergographic device, for example, a Cybex ergometer 12, in accordance with the present invention. Probe 16 is suitably fixedly mounted within the large cryogenic magnet coil 17 of the apparatus 11, within the homogeneous magnetic field thereof. The resting state of the muscle phosphorus-containing constituents is depicted by the curve shown in FIG. 3A. This curve identifies a large concentration of creatine phosphate (PCr) with a peak 19. The PCr peak 19 is shown at a chemical shift with respect to phosphoric acid ($HPO_4$) of about 5 parts per million in frequency. Repetitive contractions of the muscle, such as in performing repeated work actions, as will be presently described, causes a rapid utilization of creatine phosphate, eventually causing the PCr peak to decline, for example, to the level shown at 20 in FIG. 3B, and the formation of an equivalent amount of inorganic phosphate $P_i$ (see Equation 2, below), and its reaction with adenosine phosphate products ATP, which is immediately used in muscle function to produce ADP and inorganic phosphate (Equation 3, below), and the ADP is ultimately regenerated to ATP by oxidative phosphorylation (Equation 1, below):

Oxidative Phosphorylation:

$$ADP + P_i + NADH + 2H^+ + O_2 \rightarrow ATP + NAD + 2H_2O \quad (1)$$

"Energy Reserve":

$$Cr + ATP \leftrightarrow CrP + P_i \quad (2)$$

"Energy Currency":

$$ATP \leftrightarrow ADP + P_i \quad (3)$$

Important uses of this technique include (1) Determining if the oxygen supply to the muscle meets the needs of a function. This is the problem which is accentuated by peripheral vascular disease where the blood vessel patency is insufficient for an adequate supply of oxygen. Creatine phosphate may be deficient in the resting state, or the mitochondrial metabolism may be unable to maintain a sufficient level of creatine phosphate during a given exercise regime. (2) The second aspect is that insufficiency of the creatine phosphate and oxygen supply may be present for dealing with a given amount of exercise, for example, as in a training regime where selective exercises have increased the muscle mass and may or may not have appropriately increased the essential energy metabolism. In this case, a selective exercise can evoke changes of creatine phosphate which tell (a) if the energy metabolism is fully active, and (b) if the energy supply can sustain the muscle during a given amount of athletic work.

Particularly in the study of peripheral vascular disease, the leg muscles may be of considerably more interest. The leg can be inserted into a 7" magnet in a manner similar to FIG. 1.

The apparatus 11 is part of a NMR system which includes a pulse transmitter and receiver circuit connected to probe 16 and designed to study phosphorus metabolism at 24.3 MHz and a magnetic field of 20 kg. This circuit may be similar to that disclosed in the above-mentioned previously filed patent application Ser. No. 373,283, filed Apr. 29, 1982.

In the two cases mentioned above (arm or leg muscles) the ratio of the amplitude of the creatine phosphate to phosphate peaks may be of the order of 20:1 or greater, for resting states, whereas mild exercise gives a ratio of $PCr/P_i$ of about 6:1. This ratio can be termed the "$PCr/P_i$ index". Extreme exercise may produce massive changes of the index, such as possibly to about 1:1.

The apparatus of the present invention is therefore mainly for the purpose of obtaining biochemical information about the metabolic state, induced by work, of the patient's tissues. The chemical compounds to be particularly studied are phosphorus compounds involved in energy storage and release. The apparatus is also applicable for studies of human metabolism and disease, using NMR of sodium-23, carbon-13, fluorine-19, and probably other magnetic nucleii, including protons.

As shown in FIG. 1, the ergometer 12 is fixedly mounted adjacent to the end 13 of the magnet bore 23 opposite to the position of the subject, namely, adjacent to the left and in FIG. 1. A crank arm 14 is rigidly connected to the driveshaft 21 of the ergometer. A non-magnetic actuating lever 22 is pivotally mounted in the bore 23, for example having its midportion pivoted to a non-magnetic post element 24 rigidly secured in said bore. A non-magnetic link bar 25 drivingly connects one end of lever 22 to crank arm 14. The other end of lever 22 is in a position to be grasped by the subject's hand, as shown in FIG. 1, and to be rotated by wrist flexure, thereby causing contraction of the user's forearm muscle, located closely adjacent to probe 16.

The ergometer 12 is of a type providing output signals 23 on a visible indication screen, such as the screen of an oscilloscope, in response to rotations of the crank arm 14 produced by oscillations of the lever 22. The ergometer signals 23 represent known units of energy, such as foot pounds. The subject oscillates the lever 22 at a regular periodic rate, for example in response to a preselected periodic audible signal from the computer associated with the NMR apparatus. The subject visually observes the intensity of the muscular contractions in terms of the amplitude of the signals 23 and maintains uniformity in height of the signals by carefully controlling the excursions of the lever 22. The ergometer signals 23 can be counted and the total work done in the test can be calculated from the known foot pound values of the signals.

Figure 2:
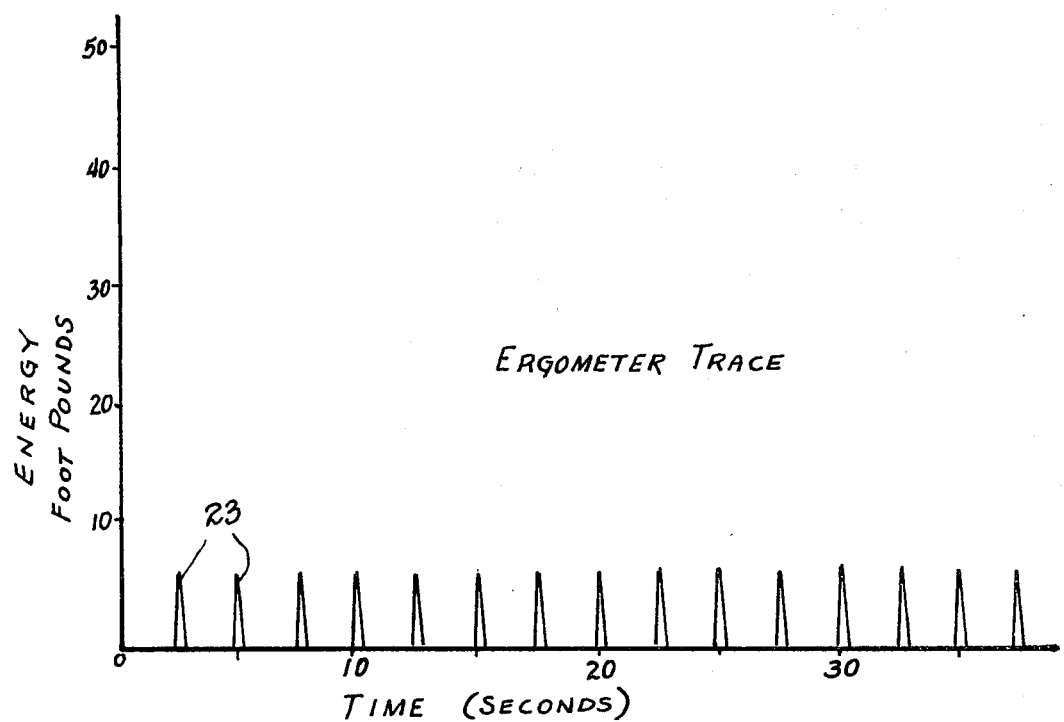
FIG. 2 is a graph comprising a typical energy output vs. time recording of the ergometer shown in FIG. 1.
Figure 4:
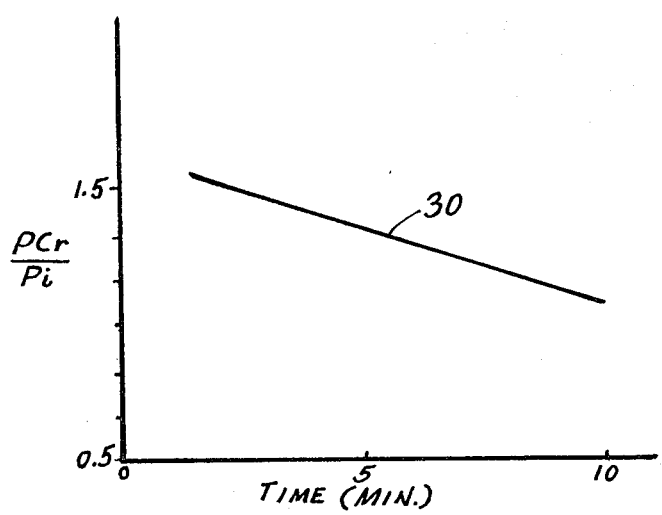
FIG. 4 is a graph showing the changes in $PCr/P_i$ plotted against time in a typical test procedure wherein the ergometer is periodically operated by the subject's arm over a period of time, in the arrangement shown in FIG. 1.

FIG. 4 represents a typical plot of $PCr/P_i$ for a test of a forearm muscle using the arrangement of FIG. 1 in the manner above described, with manual activation of the ergometer 12 at precisely 2.5-second intervals over a period of about 10 minutes, the ergometer output signals 23 being substantially as shown in FIG. 2. The sloping line 30 shows the decrease of $PCr/P_i$ with time in a manner to be normally expected with the level of exercise employed in this test, namely, a decrease of about 20%, wherein for this subject $P_i=PCr$ would substantially represent the upper limit of metabolic activity (near maximal work rate) that could be maintained relatively constant for the 10-minute interval.

Figure 5:
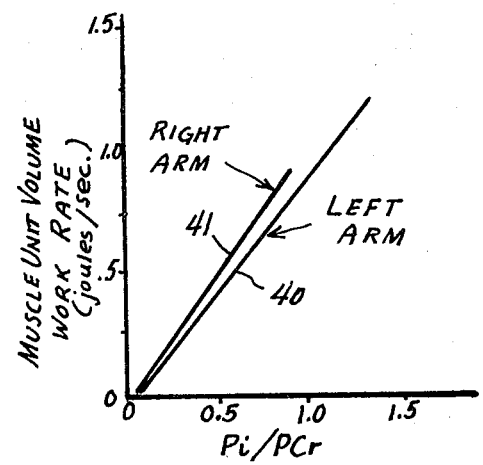
FIG. 5 is a graph showing typical plots of muscle unit volume work rate versus the ratio $P_i/PCr$ respectively for the right and left arms of a subject in tests employing the arrangement shown in FIG. 1.

FIG. 5 represents experimental data wherein work rate is plotted against $P_i/PCr$ for 6-minute steady-state work intervals. Line 40 is the plot of data for the left arm of the subject and line 41 is the plot of data for the right arm. Instead of plotting $PCr/P_i$ against the work rate per unit volume of muscle, the linearly increasing quantities of the reciprocals $P_i/PCr$ are plotted against the normalized data (work rate/unit muscle volume) for each forearm. Thus, standardized performance curves can be obtained for the bioenergetic system with normal blood flow and mitochondrial function. Deviations from these curves would result in larger values of $P_i/PCr$ for given tissue volume power outputs, as may be the case in peripheral vascular disease. Deviations from the slope of the normal in diagrams such as those of FIG. 5 may be diagnostic of various genetic and metabolic errors or deficiencies of the bioenergetic system and its associated musculature.

Various modifications within the spirit of the invention may occur to those skilled in the art. Therefore it is intended that adaptations and modifications should be comprehended within the meaning and range of equivalents of the disclosed embodiment.

What is claimed is:

1. An apparatus for determining the relationship between work output of an exercising living body member and the capability of oxidative phosphorylation of said body member, comprising a NMR analytical device of the type including a hollow magnet provided with an internal radio frequency transceiver coupling element mounted to be in electrical coupling relation to a body member inserted in the magnet, for generating curves depicting the intensities of phosphorus-containing components in the body member, including phosphocreatine (PCr) and inorganic phosphate ($P_i$), whose intensity ratio varies in accordance with the amount of work performed by the body member, an ergometer mounted adjacent to the magnet, drive means movably mounted in the magnet and being drivingly operable by the body member when said body member is in said coupling relation to said coupling element, and linkage means coupling said movable drive means to the ergometer, for registering the work performed by the body member when it operates said drive means, enabling a comparison to be made between the intensity ratio with the body member at rest and the intensity ratio following the performance of a measured amount of work by said body member.

2. The apparatus of claim 1, and wherein the drive means is pivotally mounted in the hollow magnet.

3. The apparatus of claim 1, and wherein the drive means comprises a hand lever pivotally mounted in the hollow magnet.

4. The apparatus of claim 1, and wherein the ergometer is provided with a drive arm, and wherein said linkage means comprises a link bar connecting said drive means to said drive arm.

5. The apparatus of claim 1, and wherein said drive means comprises a hand lever pivotally mounted in the hollow magnet, and wherein the linkage means comprises a drive arm on the ergometer and a link bar connecting said hand lever to said drive arm.

6. The apparatus of claim 1, and wherein said ergometer generates a visible trace comprising signals showing the work performed with each operation of the drive means, and enabling the user to control the amplitudes of the signals.

7. The apparatus of claim 1, and wherein said drive means comprises a non-magnetic hand lever pivotally mounted in the hollow magnet between the transceiver radio frequency coupling element and the end portion of the magnet adjacent to the ergometer, and wherein the linkage means comprises a drive arm on the ergometer and a non-magnetic link bar connecting said hand lever to said ergometer drive arm.

8. The apparatus of claim 7, and wherein the radio frequency coupling element comprises a probe coil fixedly mounted in the magnet in a position to receive the body member in overlying relationship thereto.

* * * * *